United States Patent [19]

Scott et al.

[11] Patent Number: 4,476,095

[45] Date of Patent: Oct. 9, 1984

[54] FLUOROMETRIC TITRATOR

[76] Inventors: Robert L. Scott, 12 Causeway La.;
Samuel Nejame, Jr., Charlesdale Rd., both of Medfield, Mass. 02052;
Charles S. Jacobs, Jr., 136 Pollard Rd., Mountain Lakes, N.J. 07046;
Charles A. Bell, 18 Wood Ridge Rd., Weston, Mass. 02193

[21] Appl. No.: 460,297

[22] Filed: Apr. 12, 1974

[51] Int. Cl.$^3$ ............................................ G01N 31/16
[52] U.S. Cl. ...................................... 422/75; 422/100;
422/102; 436/51; 436/163; 436/172; 356/244; 356/246; 250/361 R
[58] Field of Search .......................... 436/172, 163, 51; 422/75

[56] References Cited

U.S. PATENT DOCUMENTS

| | | | |
|---|---|---|---|
| 2,950,177 | 8/1960 | Brown et al. | 23/253 R |
| 3,193,358 | 7/1965 | Baruch | 23/253 R |
| 3,684,455 | 8/1972 | Vacirca et al. | 23/253 R |

OTHER PUBLICATIONS

Aloe Scientific, Catalog 103, 1952; p. 1010.
Borle et al., Anal. Chem. 40, 339, (1968).
R. L. Alexander, Jr., Clin. Chem. 17, 1171, (1971).

*Primary Examiner*—Michael S. Marcus

[57] ABSTRACT

A fluorometric titrator has means to transfer a pipette between first and second positions and a buret for a chelating agent has a reversible drive powered either by a pulse generator or an oscillator. Valve controlled means are operable to place the buret in communication with the pipette or a reservoir. In the first position of the pipette, a precise sample volume is aspirated into it by the buret, then driven by the oscillator and in its second position and with the buret drive reversed but still powered by the oscillator, the sample volume is discharged from the pipette into a cuvette in the fluorometer. On the resulting fluorescence the fluorometer output drives the pulse generator to dispense chelating agent and to operate a counter until a selected end point is reached. The pipette is then returned to its second position with the buret drive again operated by the oscillator and during the return, the buret is refilled. Both before the sample volume is aspirated, and before that volume is discharged, backlash is removed from the buret drive. The effect of hysteresis on the photocell of the fluorometer is minimized by light control also enabling the response time of the titrator to be accelerated.

36 Claims, 16 Drawing Figures

FLUOROMETRIC TITRATOR

BACKGROUND REFERENCES

"Microdetermination of Calcium in Biological Material by Automatic Fluorometric Titration", Andre B. Borle and F. Norman Briggs "Analytical Chemistry", Vol. 40, No. 2, February 1968 "Evaluation of an Automatic Calcium Titrator", Roy L. Alexander, Jr. "Clinical Chemistry", 17, 1171, (1971)

BACKGROUND OF THE INVENTION

The analysis of calcium ranks high in frequency of the tests requested in the serum/urine electrolyte series. One of the most specific tests for total calcium is the complexometer titration of a fluorescent calcium-calcein complex and because determinations of the calcium content of the body fluids are routinely required, and because the accuracy of such tests is of prime importance, investigations have been made in recent years with the objective of automating such titrations.

In such a test, a cuvette is provided with a calcein-alkaline solution with a calcein having the distinctive function of forming highly fluorescent, non-dissociated ions with the alkali earth metals and with the alkaline substance, usually potassium hydroxide, establishing a suitable pH value.

the cuvette is placed in the chamber of a fluorometer and a predetermined volume of calcium-containing sample is added to the cuvette contents. Then, while the cuvette contents are stirred and with the fluorometer in service, a chelating agent is introduced as the titrant at a controlled rate until the fluorescence is quenched. At the present time, either EDTA (Ethylene-Diamine tetra acetic acid) or EGTA (ethylene glycol tetra-acetic acid) may be used as both quantitatively bind the metal in a mole-to-mole relationship although EGTA is preferred as it provides additional specificity, due to its greater affinity for calcium than for magnesium at a high pH level, 13, for example.

The fluorometer is provided with filters appropriate for the rather close relationship between the excitation and emission wave lengths, 495 nanometers and 516 nanometers, respectively. The end point of the titration is marked by the reduction in the fluorescence of the cuvette contents to a predetermined value. Assuming that the precise volume of the titrant used is known, the calcium content of the sample is the same as the molar equivalent quantity of the titrant that was used. Desirably, the delivery of the titrant to the cuvette is stopped when the end point is reached. To this end, a motorized buret is used that is driven by a stepper motor with the pulses by which it is powered also providing a basis for a count that represents the delivered volume of the chelating agent.

While the automation of any part of fluorometric titrations has substantial potential advantages over those effected manually, in general, rapidity, maximum accuracy, and a high degree of reproducibility, these advantages have not been fully attained. For examples, the selection of the volume of a sample required for a test have remained dependent on the ability and care of the individual or individuals making the analysis, and error-producing factors have remained troublesome such as the fact that end points of the titrations have not been stable and reproducible, and errors are introduced due to backlash present in the buret drives.

THE PRESENT INVENTION

The general objectives of the present invention are to provide a fluorometric titrator adapted to be automatic or semiautomatic in its operation and providing increased test accuracy, a reduction in the time and manual effort required in determining the total calcium in biological fluids, and enabling the manual operations to be limited to the preparation of a proper calcein-alkaline solution in a cuvette, the placing of the cuvette in the chamber of the fluorometer, and the proper positioning of a sample container relative to the titrator. While the invention is herein discussed with particular reference to analyses for total calcium, it is not to be regarded as limited thereto. It is equally well adapted for analysis for total magnesium, for one example, once it is discovered that a chelating agent has or can be made to have a greater affinity for magnesium than for calcium under the right pH conditions. With the titrants mentioned and with the pH at about 12, total magnesium can be determined if no calcium is present. Magnesium and calcium can also both be measured with the mentioned titrants with the pH at about 12 and, subsequently calcium only measured with the pH value at 13 with the magnesium determinable by subtraction.

In accordance with the invention, these general objectives are attained with a fluorometric titrator having a cuvette in the chamber of its fluorometer containing an appropriate calcein-alkaline solution and a stirrer in the cuvette.

One objective of the invention is to minimize the effect of hysteresis in the photocell either by maintaining the light, as sensed by the photocell at a substantially constant level at all times or by establishing a constant level of cell illumination between titrations.

Another objective of the invention is to make automatic the aspiration of a sample and its transfer into the cuvette. A device such as a pipette is carried by reversible transfer means between first and second positions. Sample control means are provided to aspirate into the device in its first position a precise sample volume and to discharge that volume into the cuvette in its second position. The titrator also includes means operable by the output of the fluorometer in response to the fluorescence resulting from the discharge of the sample volume into the cuvette to deliver chelating agent into the cuvette and to produce an indication of the value of a chemical contained in the sample with the delivery means terminated by a detector when the fluorescence has been reduced to a predetermined level selected as the end point of the test. A further objective is to use the detection of the end point to initiate the return of the device to its first position. In practice, the sample control means includes a reversible pumping means and both before the aspiration of the sample volume and before the discharge thereof, means are provided to remove backlash therefrom, an important feature of the invention.

Another objective of the invention is to employ the pumping means for the chelating agent as the pumping means for aspirating and discharging the precise sample volume. This objective is attained by providing a buret having a reversible drive for the delivery of the chelating agent and utilizing a valve control operable to place the buret in communication with the device or with a reservoir. The buret is driven by means operated by pulses, a stepper motor, powered either by a pulse generator driven by the fluorometer or by an oscillator as a preferred example, or as another example, a variable speed motor provided with means to interrupt, as its drive shaft turns to operate the buret, a light path to a photodetector thus to yield electrical operating pulses. On the return of the device to its first position, the buret is driven by the oscillator to first withdraw whatever volume of chelating agent from the reservoir is necessary to recharge it and simultaneously removing backlash from the buret drive and then, when the device is in its first position, to aspirate the precise sample volume. At the start of the next titration and before the device reaches its second position, enough chelating agent is pumped back to the reservoir to remove backlash from the pumping means when driven in a discharging direction. The term "backlash" as used herein means both backlash from the drive and any hysteresis in the buret.

Another objective of the invention is to ensure accuracy in the aspiration of the sample volumes. For this purpose, the pumping means of the sample control means is driven by the oscillator under the control of a timer operable for a precise time interval but provided with an adjustable control enabling the interval to be varied for the purpose of calibrating the titrator. The titrator has, of course, readout means for providing test information derived from and based on a count derived from the pulse generator. By titrating a known volume of a sample of a known value, a comparison of the readout value at the end of the titration of that sample with the known value determines accuracy with any appreciable difference corrected by varying the precise time interval to vary the aspirated volume until the known and readout values match.

A particular objective of the invention is to enable different sample volumes to be provided. To accomplish this result, the output of the oscillator to the stepper motor includes means for converting the number of pulses delivered by the oscillator under the control of the timer to a predetermined different number thus to vary the operation of the pulse generator thereby to vary the aspirated volume without changing the adjustment of the timer.

In practice, a second timer is used to power the oscillator when the buret is driven to remove backlash and to recharge it and provides a time interval different from that required for the aspiration of the sample volume. A particular objective of the invention is to provide a barrier between the chelating agent and the aspirated sample volume and this is accomplished by operating the second timer after the buret has been recharged then to aspirate an air bubble into the device and, again, to discharge that air bubble after the discharge of the sample volume into the cuvette.

Yet another objective of the invention is to eliminate end point drift as a cause of error. Such drifting is due to such causes as (1) aging of chemicals, (2) temperature drift, and (3) contamination of the cuvette contents and its effects are compensated for by providing that, at least after the first of a series of titrations, the starting point of each titration is the same as the end point of the previous titration or by using as the starting point the conditions existing immediately prior to the addition of the sample to the cuvette as by subjecting the end point detector circuit to a predetermined initial voltage, desirably but not necessarily, by electrical means.

Another objective of the invention is to provide novel titrator components that are used in titrations in accordance with the invention and may also be used to advantage in other combinations.

One such component is the buret which meets the requirements of increased accuracy by providing a threaded drive of a micrometer type, i.e., one in which the two threaded parts are carefully interfitted and mated to ensure smooth and uniform relative movement, and by utilizing a positive displacement of the chelating agent from the cup of the buret thus to avoid the drag attendant the use of a mated piston and cylinder while that part of the piston that is a slidable fit within the cylinder rearwardly of the cup is of a material minimizing friction. With the diameter of the buret piston, the step by which it is advanced or retracted, the gear ratio and the screw lead being selected to provide pulse-to-volume steps in a convenient ratio, for example, one pulse equalling 0.2 microliters, any convenient whole number volume can be accurately aspirated or dispensed by the appropriate number of pulses.

Another such component is the pipette transfer which is driven by a reversible motor between the first and second positions of the device with the device extending downwardly and having a predetermined angular disposition at each of said positions.

Yet another of the components is a stirrer that includes an arm extending downwardly into the cuvette and reciprocated transversely as by a vibrator in a vertical plane inclusive of the axis of the path of the light beam from the fluorometer lamp and having the section that is in that path so narrow with respect to the plane in which it is reciprocated that it has no appreciable adverse affect on the action of the fluorometer while stirring the buret contents vigorously below that level without creating any detectable vortex affect and/or air bubbles associated therewith.

Additional objectives of the invention will be apparent from the description of the preferred embodiment thereof.

BRIEF DESCRIPTION OF THE DRAWINGS

In the accompanying drawings, a preferred embodiment of the invention is illustrated with FIG. 1 a schematic view of the titrator.

THE PREFERRED EMBODIMENT OF THE INVENTION

Before detailing the fluorometric titrator, it will be helpful to indicate its essential mechanical components and the general mode of its operation.

Figure 1:
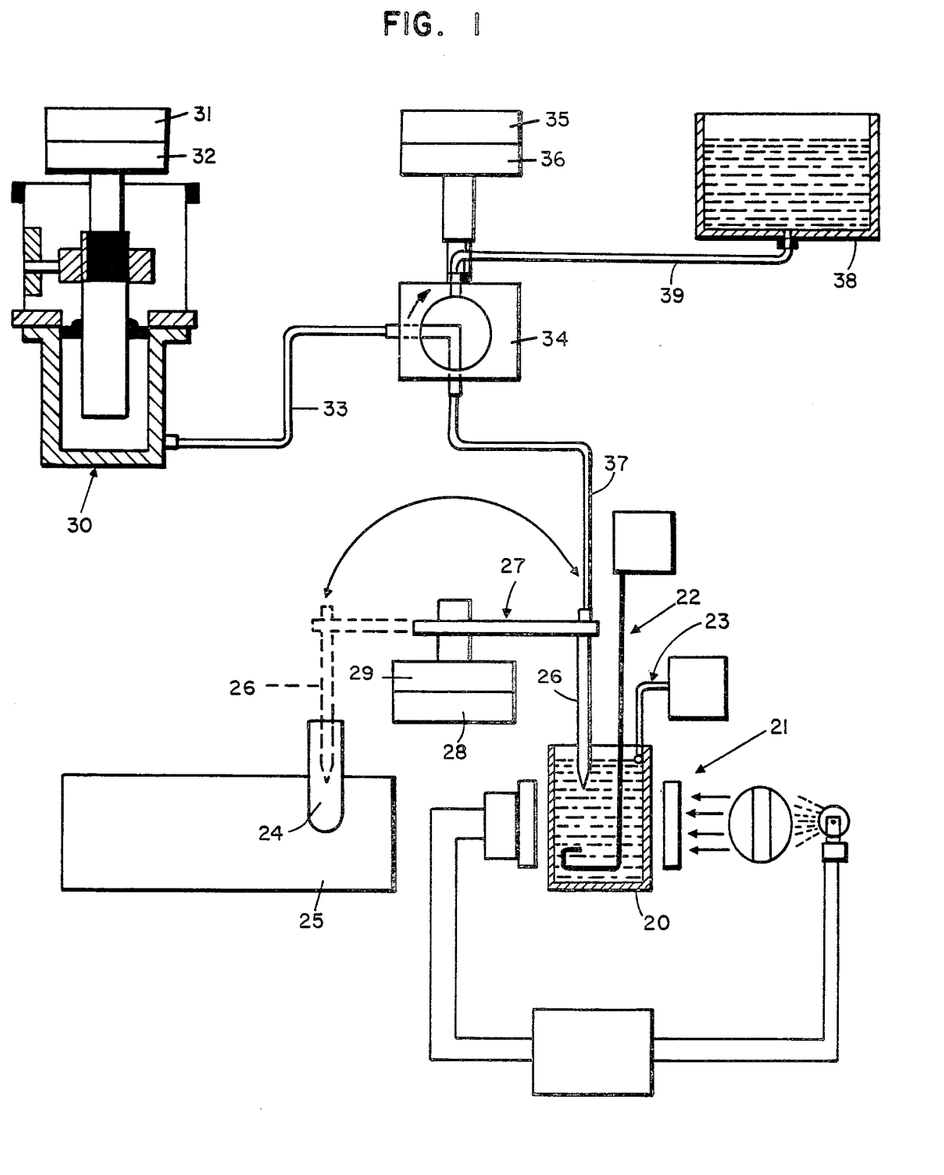
Figure 5:
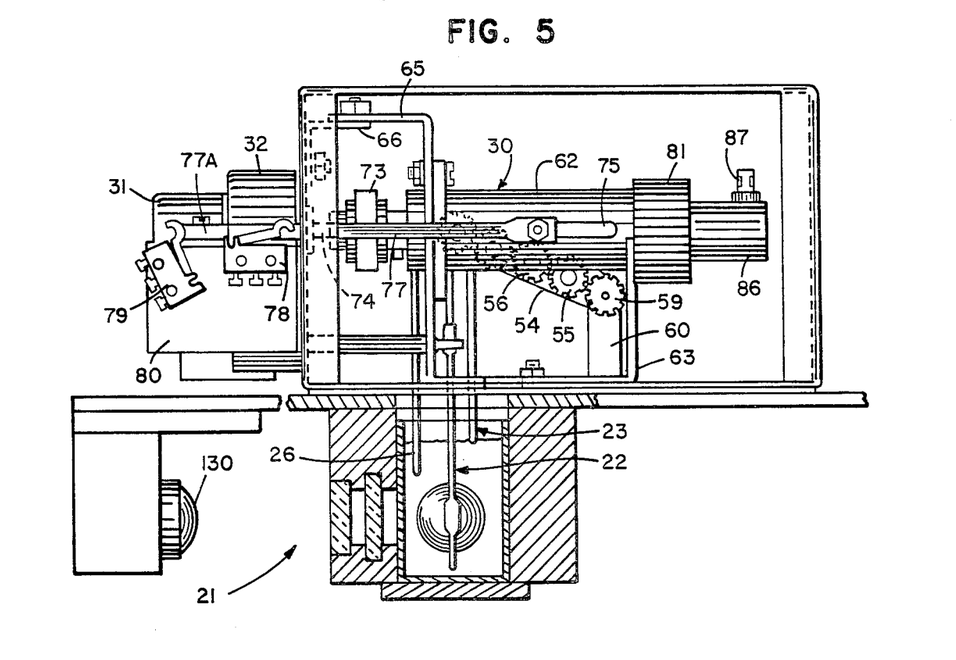
FIG. 5 is a side view of the chamber looking towards the wall shown in FIG. 3.
Figure 6:
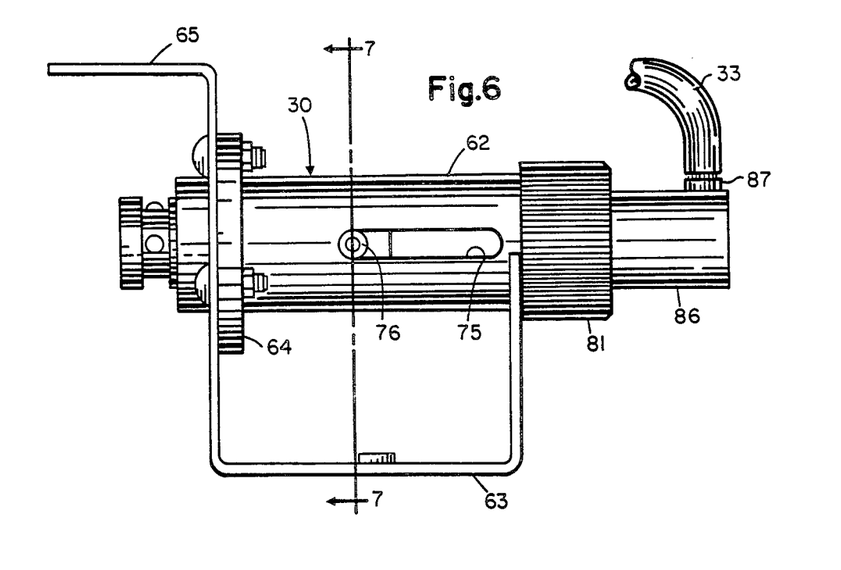
FIG. 6 is a side view of the buret.
Figure 7:
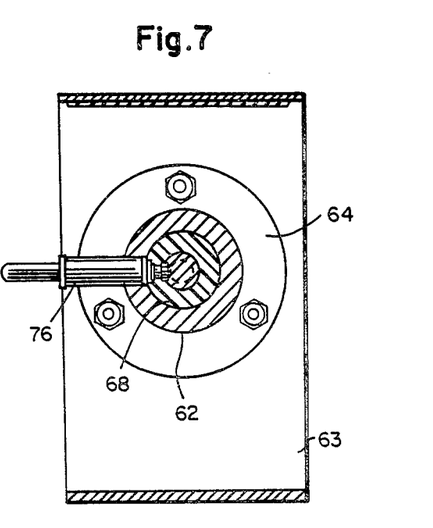
FIG. 7 is a section taken approximately along the indicated lines 7—7 of FIG. 6.

Reference is first made to FIG. 1 wherein a cuvette 20 is located in the chamber C of a fluorometer, generally indicated at 21. The cuvette 20, in practice, is entered into the chamber from below and, as it is positioned therein, it receives within it a stirrer, generally indicated at 22 and a liquid level probe, generally indicated at 23. The cuvette 20 is filled, prior to its introduction into the fluorometer chamber with a calcein-alkaline solution, tha alkaline, in the case of a test for calcium, in practice, being potassium hydroxide and the pH value of the solution typically 13. the cuvette 20 is molded from any suitably inert transparent material with a flat bottom and the side wall is at right angles thereto and it may be either circular or square in cross section. The cuvette is a free but close fit in the fluorometer chamber C and in a recess in the holder H threaded in the bottom of the chamber C, see FIGS. 5 and 9.

A sample-containing tube 24 is indicated as being held in a certain position 25 by a turntable, for one example, or by the technician as another example. A pipette 26 is supported by a transfer, generally indicated at 27 and driven between two extreme positions by a reversible motor 28 through a transmission 29, the first or sample-receiving position presents the tip of the pipette within the tube 24 held as at 25 and the second or discharging position places the tip in the cuvette 20.

A buret, generally indicated at 30, is provided with a drive consisting of a reversible stepper motor 31 and a transmission 32. A length of tubing 33 places the buret 30 in communication with a valve 34 rotatable between first and second positions by a reversible motor 35 through a transmission 36. In the first position of the valve 34, it places the buret 30 in communication with the pipette 26, the appropriate port of the valve 34 and the pipette 26 being interconnected by a length of flexible tubing 37 that permits the movement of the pipette from one extreme position to another. In the second position of the valve 34, the buret 30 is placed in communication with a reservoir 38 for the chelating agent, preferably EGTA in the case of calcium titrations, the appropriate port of the valve 34 and the reservoir 38 being interconnected by tubing 39. The valve ports to which the tubing 37 and 39 are connected are shown as each spaced 90° apart relative to the port to which the tubing 33 is connected. In practice, the tubing has an inside diameter in the range of 0.020 to 0.100 of an inch.

The general mode of operation may best be summarized by assuming the end of the test with the pipette 26 still within the cuvette 20. At the end of the test, the pipette is returned to its first position and during its return, the valve 34 is first set in its second position and the buret 30 driven in an aspirating direction to withdraw a replacement supply of the chelating agent from the reservoir 38, if such is needed, and, in any event, to aspirate enough of the chelating agent to remove backlash. The valve 34 is then returned toward its first position and the buret 30 again preferably operated to aspirate air to provide a bubble between the tip of the pipette 26 and the valve 34 as a barrier between the chelating agent and the next sample volume to be aspirated.

A precise sample volume is aspirated into the pipette 26 when it is in its first position by driving the buret in an aspirating direction for a precise time interval, the valve 34 remaining in its first position.

After the sample volume is aspirated, another titration is initiating by returning the pipette 26 to its second position and during its return, the valve 34 is first shifted into its second position and the buret 30 driven in a discharging direction to pump back to the reservoir 38 enough of the chelating agent to remove the backlash from the now reversed drive, and the valve 34 is then returned to its first position. When the pipette 26 reaches its second position, the buret 30 is driven to discharge the sample and the air bubble. The operation of the buret, except during a titration, is effected by means later to be detailed. As fluorescence then results, the fluorometer 21 is operative, by different means aslo later to be described, to so drive the stepper motor 31 that the chelating agent is dispensed until the selected end point of the titration has been reached after which the return of the pipette to its first position is initiated.

Figure 2:
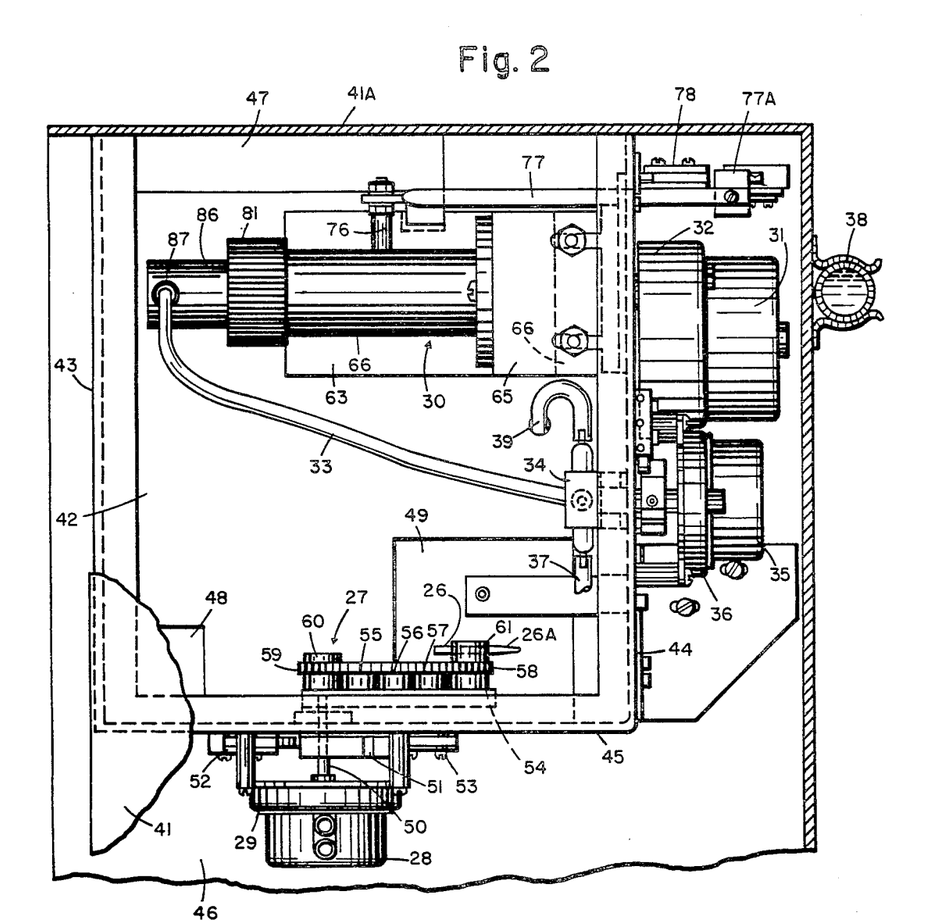
FIG. 2 is a fragmentary plan view of the chamber of the instrument in which the buret, valve and pipette transfer components are housed.
Figure 3:
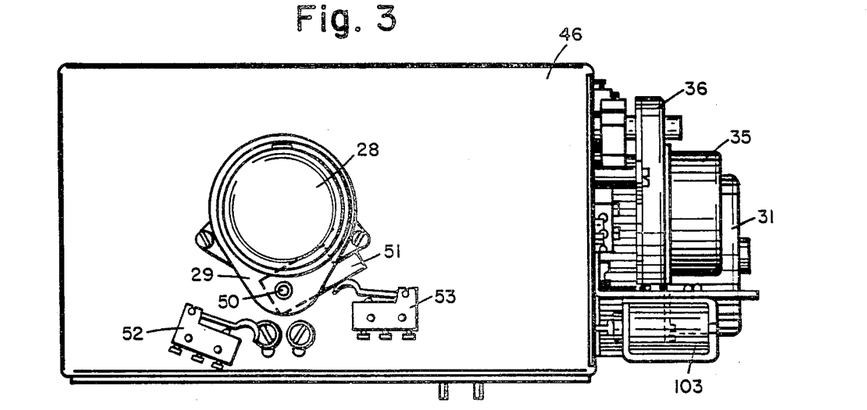
FIG. 3 is a view of the outer face of the side wall of the chamber.
Figure 4:
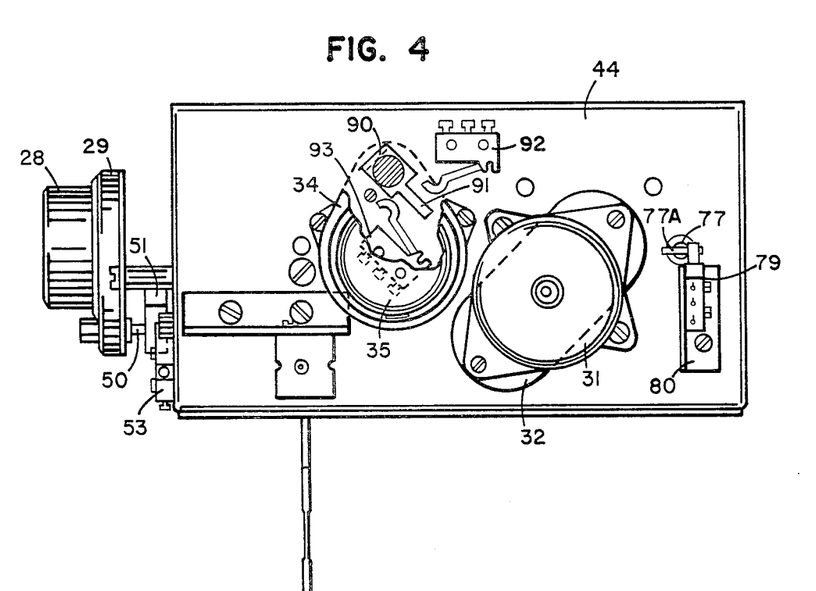
FIG. 4 is a view of the rear face of the rear wall of the chamber.

At this point, certain components of the titrator are detailed and reference is made to FIGS. 2–5. In FIG. 2, a portion of the generally indicated cabinet 40 of the titrator is shown with its cover 41 and its side wall 41A broken away to show the chamber 42 and its front and back walls 43 and 44, respectively, the cover and the wall 45 separating the chamber 42 from the chamber 46 in which the major portion of the circuitry is located. It will be appreciated that with the cover 41 in place, the chamber 42 is suitably light and liquid tight except for the port 47 adjacent the cover wall 41A, the port 48 in its floor downwardly through which the tip of the pipette 26 extends in its first position, the floor also having a port 49 in which the cuvette 20 is exposed to receive the pipette when in its second position.

The motor 28 and transmission 29 of the transfer 27 are located in the chamber 46 and supported by the wall 45 and the shaft 50 extends through a bushing (not shown) in the wall 45. The shaft 50 has, in the chamber 46, one end of an arm 51 fixed thereon to close a normally open switch 53 when the pipette 26 is in its first position and normally open switch 52 when the pipette is in its second position. An arm 54 is fixed on the end of the shaft 50 within the chamber 42 and carries a gear train shown as consisting of four gears 55, 56, 57, and 58 rotatably mounted thereon. The gear 55 is in mesh with a gear 59 coaxial with the motor shaft 50 and fixed in a mount 60 on the chamber floor. The gear 58 includes a hub 61 having a transverse bore through which extends the angularly disposed end portion 26A with the flexible tubing 37 secured to its extremity. Because of the gear train, the pipette 26 is always held in predetermined position at either limit of travel of the transfer 27 and it will be noted that the arm 54 swings through an arc of approximately 180° between the two positions of the pipette 26.

Turning now to FIGS. 2 and 5–8, it will be seen that the buret 30 has a barrel 62 supported near its outer end in the outer end wall of a U-shaped mount 63 secured to the floor of the chamber 42 with the barrel extending rearwardly through the other end wall of the mount with its annular flange 64 bolted thereto and with said other end wall terminating in a flange 65 bolted to a shoulder 66 fixed on the inner surface of the wall 44. In practice, the mount 63 positions the barrel 62 so that it is forwardly and slightly upwardly inclined to ensure that air bubbles will not be trapped in the buret.

Figure 8:
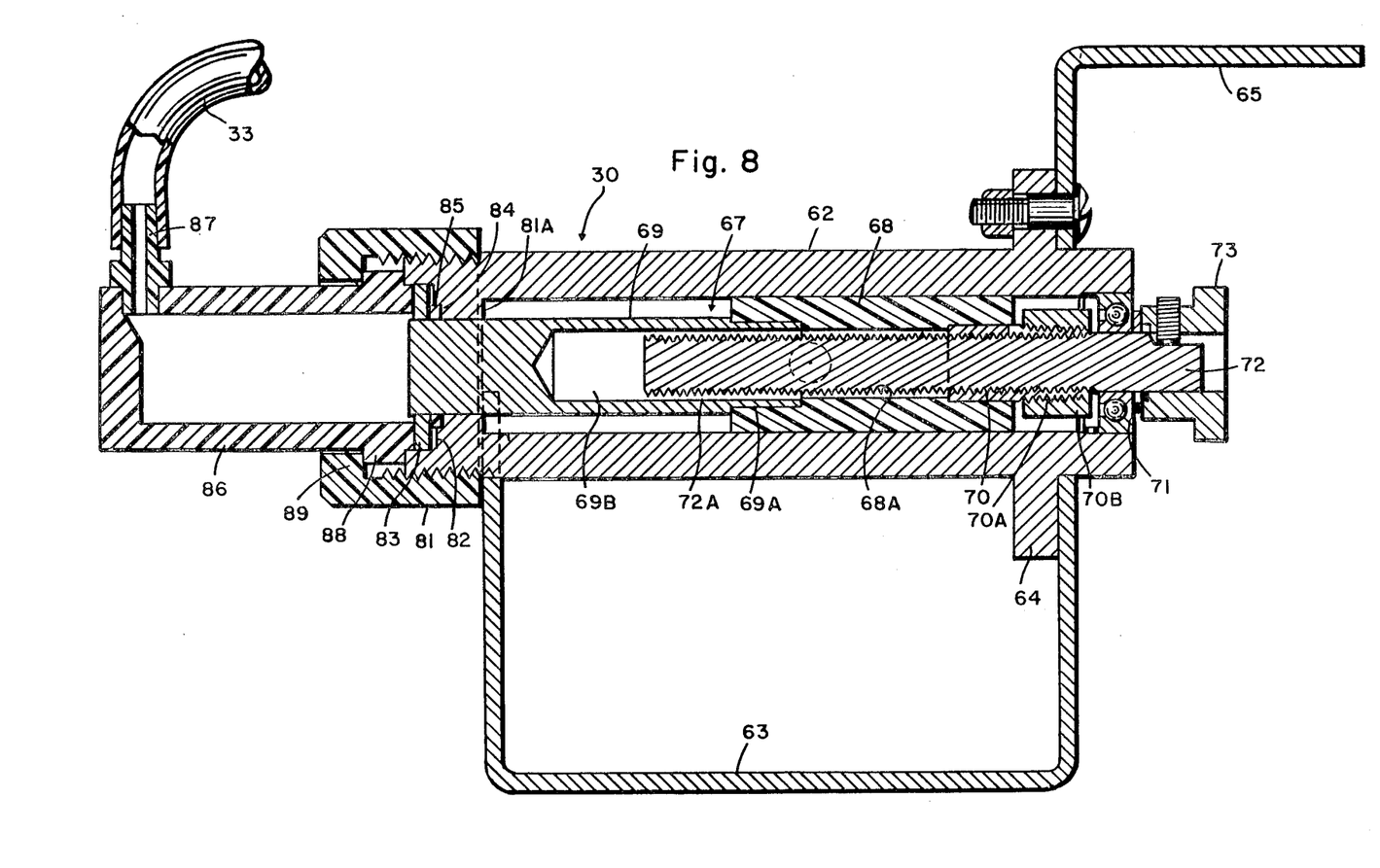
FIG. 8 is a section on an increase in scale, taken lengthwise of the buret.

A piston, generally indicated at 67 and best seen in FIG. 8, includes a first section 68 and a second section 69. The piston section 68 is a sliding fit in the barrel 62 and is desirably molded from a self-lubricating material such as Teflon and has an axial bore 68A having a counterbore in its rear end in which a micrometer type of nut 70 is a press fit having its jaws 70A externally threaded to receive the clamping nut 70B. The piston section 69 is of a substantially smaller diameter and has the diameter of its inner end further reduced to provide a shouldered end 69A that is a press fit in a counterbore in the outer end of the bore 68A. The piston section 69 has an axial bore 69B opening through its rear or inner end.

A ball bearing unit 71 is fixed in the rear end of the barrel 62 in support of a shaft 72 having a threaded section 72A threaded through the micrometer nut 70. A coupling 73 locked to the shaft 72 connects it to the driven shaft 74 of the transmission 32. The shaft 74 extends through a bushing, not shown, in the wall 44 and both the transmission 32 and the stepper motor 31 are mounted on the rear side thereof. The threaded section 72A is of such length as to provide a suitable piston stroke as the shaft 72 is rotated and, accordingly, when the piston section 69 is fully retracted, the free end of the threaded section 72A is within the bore 69B and the piston section 69. It should be here noted that the internal threads of the nut 70 and the threads of the shaft section 72A are those characteristic of those used in micrometers, that is they are carefully interfitted and mated to ensure uniform piston travel.

The barrel 62 has a slot 75 extending lengthwise thereof to receive an arm 76 threaded into the piston section 68 with the arm 76 holding it against turning as the shaft 72 is rotated in one direction or the other and with the length of the slot 75 permitting the wanted piston travel. The arm 76 supports a rod 77, see FIGS. 2 and 5, extending through and slidably supported by a bushing, not shown, in the chamber wall 44 with its extremity provided with an actuator 77A engageable with a normally open limit switch 78 that is closed when the piston 67 is fully advanced and a normally open reference switch 79 that is closed when the piston 67 is retracted to an extent indicative of the buret containing an adequate volume of the chelating agent for a titration. The switches 78 and 79 are secured to a mount 80 on the rear side of the wall 44.

The outer end of the barrel 62 is externally threaded to receive a threaded clamping ring 81 and has an internal annular shoulder 81A through which the piston section 60 freely extends. The shoulder 81A has a first counterbore 82 which receives a washer 83 and a second counterbore 84 in which a seal 85, typically a so-called O-ring, slidably receives and seals the piston section 69 with negligible friction.

A cylindrical cup 86 has in its closed outer end a port in the form of an upwardly disposed nipple 87 to which the tubing 33 is attached. The open end of the cup 86 is dimensioned to enter the counterbore 82 and seat the washer 83 against the seal 85 and has an external flange 88 to be engaged by the internal shoulder 89 of the clamping ring 81 enabling the cup 86 to be securely locked and sealed against the outer end of the barrel 62 by suitably tightening the clamping ring 81.

The valve 34 is mounted on the inner surface of the wall 44 near the top thereof and the motor 35 and its transmission 36 are mounted on the rear surface thereof with the shaft 90 by which the valve is shifted between its two positions extending through a bushing, not shown, in the wall 44. The shaft 90 has an arm 91 engageable with the normally open switches 92 and 93 as the valve is turned 90° in one direction or the other to establish a selected one of its two operative positions.

Figures 9, 9A:
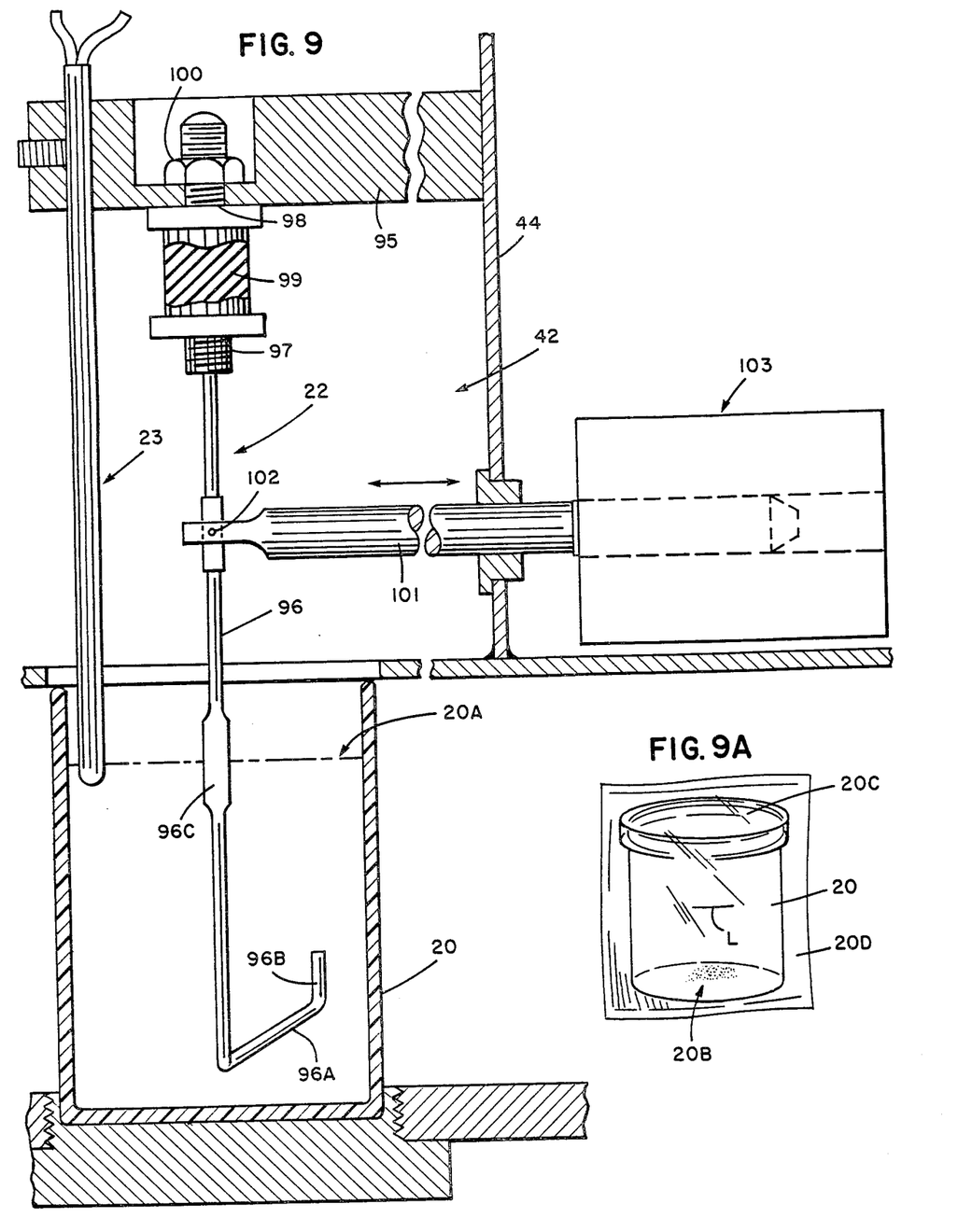
FIG. 9 is a section, on an increase in scale, taken vertically through the cuvette and showing the stirrer.
FIG. 9A is a plan view of a cuvette containing premixed chemicals, and packaged in a sealed envelope.

The rear wall 44 is provided with a support 95 extending forwardly over the cuvette 20 but close to one side thereof. The support 95 supports the liquid level probe 23 and also the stirrer 22, the details of which are shown in FIG. 9.

The stirrer 22 consists of a rod 96 having at its upper end a flexible connection with the support 95, the connection consisting of flanged threaded members 97 and 98 molded into the ends of an intermediate rubber section 99, the member 97 connected to the rod 96 and the member 98 extending upwardly through the support 95 and locked thereto by a nut 100. The rod 96 is dimensioned to extend substantially to the bottom of the cuvette 20 positioned in the chamber of the fluorometer and the rod has a transversely disposed portion 96A having an upturned end portion 96B. The beam path of the fluorometer through the cuvette is generally indicated at 20A. An arm 101 is connected to the rod 96 as at 102 and extends through a bushing in the wall 44 where it is connected to vibrating means, conveniently a solenoid 103. While it is desirable that the contents of the cuvette be thoroughly stirred throughout the test, air bubbles or an eddy effect would adversely affect the accuracy of the test results. For that reason, the rod 96 is flattened as at 96C in a zone inclusive of the beam path with the purpose of rendering the stirrer sufficiently thin in the plane in which the rod 96 is vibrated as to avoid such undesirable effects.

One particular advantage of the titrator as thus far described is that, except for the leads of the liquid level probe, the chamber 42 is free of electrical connections and wires, and said leads are, in practice, completely sealed. As a consequence, the chamber 42 may be flushed if and when necessary or drained if spillage occurs therein, in any case without damaging the circuitry.

Figure 10:
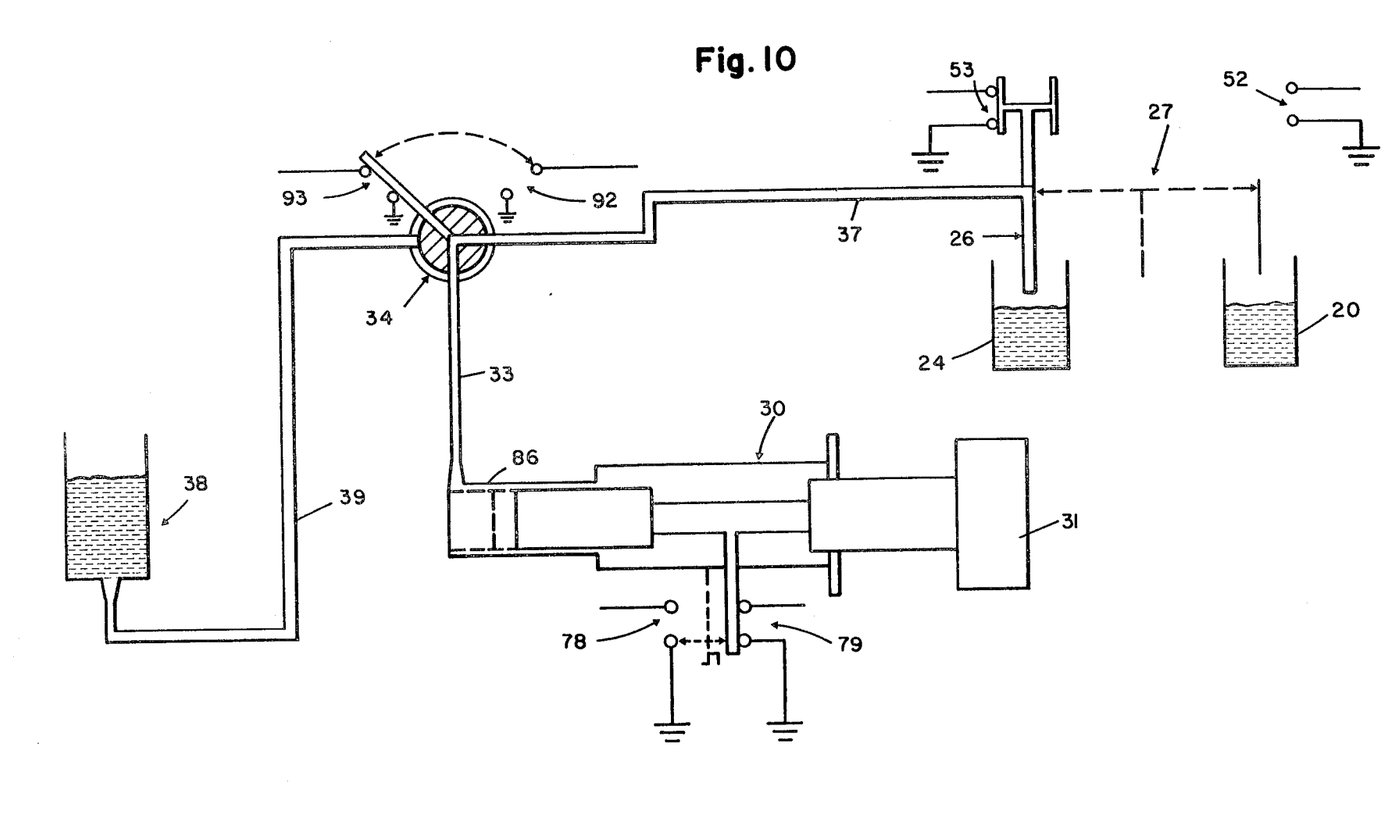
FIG. 10 is a schematic view of the titrator showing the valve, the pipette and the transfer and the switches operated thereby.
Figure 11:
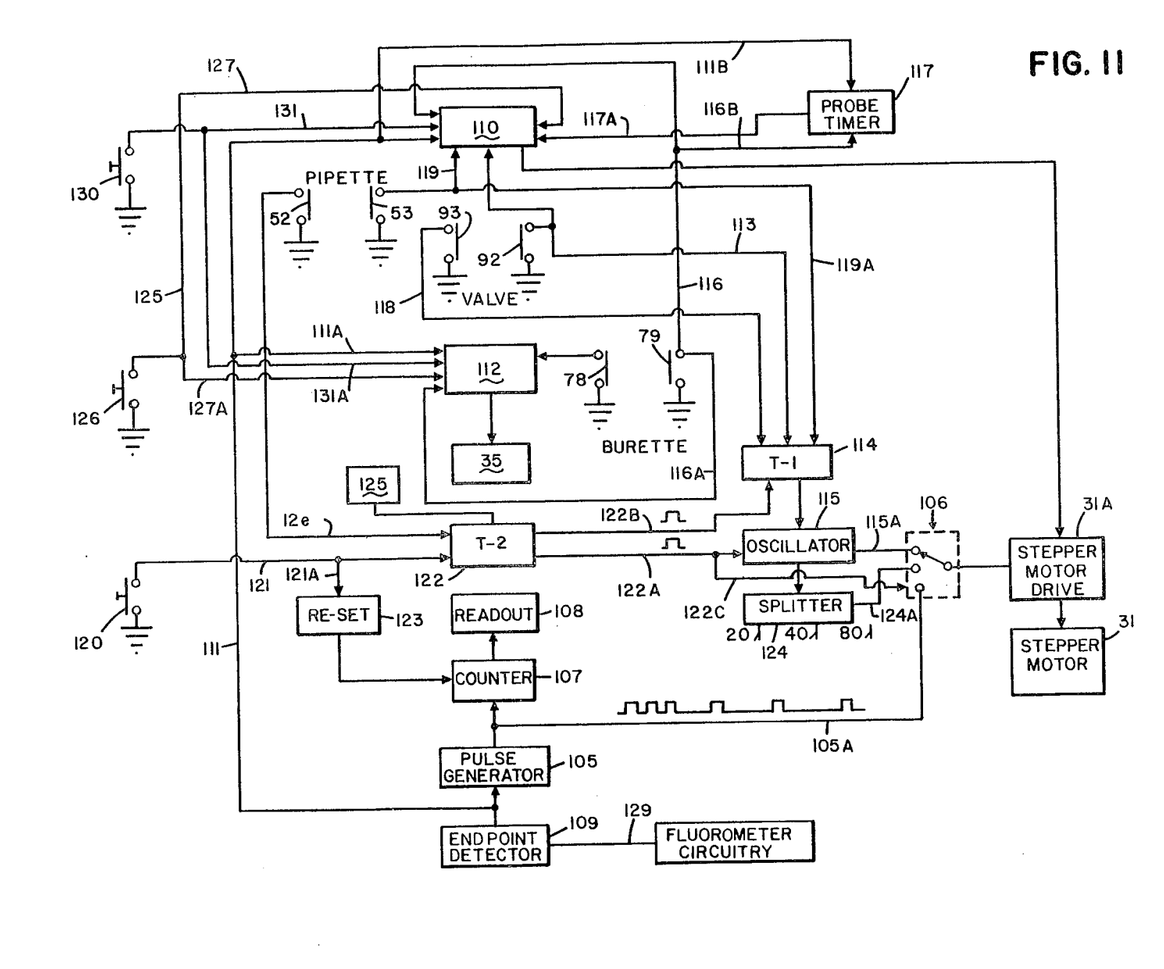
FIG. 11 is a block diagram of the circuitry.

As the general mode of operation has been summarized and the mechanical components of the titrator and their arrangement detailed, a more detailed description of the operation of the titrator is now set forth in connection with circuitry that permits titrations to be made automatically after a precise sample volume has been aspirated. Reference is made to FIGS. 10 and 11, with FIG. 10 showing various components arranged somewhat differently than in FIG. 1 in order that the switches associated with the buret 30, the transfer 27, and the valve 34 may be schematically shown and their different operating positions and those of the buret, transfer and the valve indicated. In FIG. 11, the circuitry is shown largely in block form as the components are conventional and commercially available so that, with the exception of that part of the circuitry shown in FIGS. 12–15, further details of circuitry are unnecessary.

The preferred operation of the titrator and the circuitry may be conveniently described with reference to stages, desirably assuming that a titration is taking place as the first stage.

1. During a titration, the valve 34 is in its first position (connecting the pipette to the buret with the switch 93 closed) and the buret 30 is driven in a dispensing direction by the stepper motor 31 and both the limit switch 78 and the reference switch 79 are open. The pipette 26 is in its second position (its tip in the cuvette 20 with the switch 52 closed). The stepper motor 31 is driven by a pulse generator 105 with its lead 105A connected to the stepper motor drive 31A, a Haydon Motor Circuit, for example, by the switching means generally indicated at 106 and detailed in FIG. 14. The pulse generator 105 also drives a counter 107 operating a readout device 108 with the operation of the pulse generator 105 under the control of an end point detector 109 by which, when the fluorescence has been reduced to a predetermined value selected as the end point of the test, the pulse generator 105 is stopped and by which the return of the pipette 26 to its first, sample-receiving position is initiated with the buret 30 refilled, backlash removed, and an air bubble aspirated during that transfer.

2. The block 110 of the circuitry represents a conventional reversing control for establishing the direction the motors 28 and 31 will operate and, additionally effecting the operation of the valve-shifting motor 35 on each such directional change. When the detector 109 stops the pulse generator 105 it also, via a connection 111, sets the reversing control 110 so that the motor 28 drives the transfer 27 to return the pipette to the first, sample-receiving position and to provide that the motor 31, when energized, will drive the buret 30 in its aspirating direction.

The block 112 represents a conventional reversing control for establishing the direction the motor 35 will operate and for effecting its operation on each such directional change. The connection 111 includes a branch connection 111A with the reversing control 112 so that at the end point of a titration, the valve 34 is shifted into its second position connecting the buret 30 to the reservoir 38 and closing the switch 92.

It should be here noted that the motor and drives in control of the valve 34 and the pipette transfer 27 are identical. As previously stated, the pipette is transferred through an arc of about 180° while the valve 34 is turned through 90°. The valve 34 may, therefore, be shifted twice during the transfer of the pipette in either direction.

The switch 92, when thus actuated, closes a lead 113 to a timer 114, such as a NE555 timer manufactured by Signetics Integrated Circuits Co., which timer then effects the connection of the output 115A of the oscillator 115 to the stepper motor drive 31A through switching means 106. Such a timer has lines both to trigger and to inhibit its operation. The stepper motor 31 is thus driven for a precise time interval T-1, 0.25 sec., for example.

During the interval T-1 during which the timer 114 is operative, enough chelating agent is withdrawn from the reservoir 38 to remove backlash from the buret drive until its direction is again reversed. If the buret switch 79 is not then closed, as it is when the buret 30 is recharged, the valve 34 remains in its second position keeping the timer 114 in operation until the buret is recharged. When the buret switch 79 closes, its connection 116 to the control 110 maintains the direction in which the buret 30 and the transfer 27 move but the branch connection 116A with the control 112 reverses the direction of the valve motor 35 to place the valve in its first position to again place the pipette 26 in communication with the buret 30. If necessary or desired to insure an adequate time for the recharging of the buret, the transfer may be halted until the switch 79 closes or its return rate may be slowed.

For that reason, the connection 111 from the end point detector 109 has a branch 11B to a timer 117 to effect the operation of the motor 28 through a connection 117A with the control unit 110 for a period equal to one-half the time required to transfer the pipette 26 back to its first position. A branch 116B of the connection 116 to the timer 117 again operates it when the switch 92 is closed for a like period thereby to complete the return of the pipette 26 to its first position with the buret recharged. The timer 117 may be a NE555 manufactured by the above referred-to Signetics Integrated Circuits Co.

With the valve 34 in its first position, the switch 93 in control of the connection 118 with the timer 114 closes thereby to operate it for the interval T-1 thereby to aspirate a small volume of air that forms an air bubble between the valve 34 and the pipette 26 as a barrier between the chelating agent and the next sample.

When the transfer 27 returns the pipette 26 to its first, sample-receiving position, its connection 119 with the control 110 opens the motor circuits and its connection 119A to the inhibit line of the timer 114 preventing its operation while the pipette 26 is in its first position. The titrator is now set for another sample aspiration.

3. When another test is to be made, the switch 120 closes a lead 121 to a timer 122 and a branch 121A to a conventional reset 123 in control of the counter 107 and operable to return the readout 108 to zero as is conventional.

The timer 122 has a connection 122A by which it connects for a precise time T-1 the output of the oscillator 115 to a device 124 adjustable to provide for the selection of sample volumes of different sizes. The device 124 is shown in more detail in FIG. 13 but it is connected by a lead 124A to the switching means 106. In practice, the precise sample volume is 80 $\mu$l. but the device 124 is adjustable to provide that sample volume of 40 to 20 $\mu$l., for examples, may be aspirated without readjusting the timer 122.

It should be noted that the timer 122 is provided with an adjustable control 125, a potentiometer, adapted to adjust the timer 122 to properly calibrate the titrator. This may be done by titrating a sample of a known and measured volume and of a known calcium content. The readout at the end of the titration of that sample is then compared with its known value and any difference corrected by means of the control 125 to lengthen or shorten the precise time interval T-2, say 2 secs., to vary the aspirated volume to ensure that on the titration of another sample of known value but of different volume the readout and known values would be the same.

4. When the aspirated sample is to be subjected to analysis, the switch 126 in control of a lead 127 is closed to the reversing control 110, reversing the motor 28 so that it now drives the transfer 27 in a direction to advance the pipette 26 to its second position in which it is in the cuvette 20 and setting the stepper motor 31 so that it will be driven to operate the buret 30 in a dispensing direction. A branch lead 127A to the reversing control 112 causes it to operate the motor 35 to set the valve 34 in its second position closing the switch 92 with the result that the timer 114 is again in service to control the output of the oscillator 115 to drive the stepper motor 31 for the predetermined time T-1, pumping back to the reservoir 38 enough of the chelating agent again to remove backlash.

When the pipette 26 reaches its second position, the transfer switch 52 closes a lead 128 to the timer 122 thereby to connect the output of oscillator 115 to the stepper motor 31 for an interval T-2 discharging the sample and then by reason of its connection 122B with the timer 114, triggering the timer 114 to effect the operation of the oscillator 115 for an interval T-1 thereby to effect the discharge of the air bubble. With the sample dispensed fluorescence results in the cuvette 20 to initiate the titration.

Figure 12:
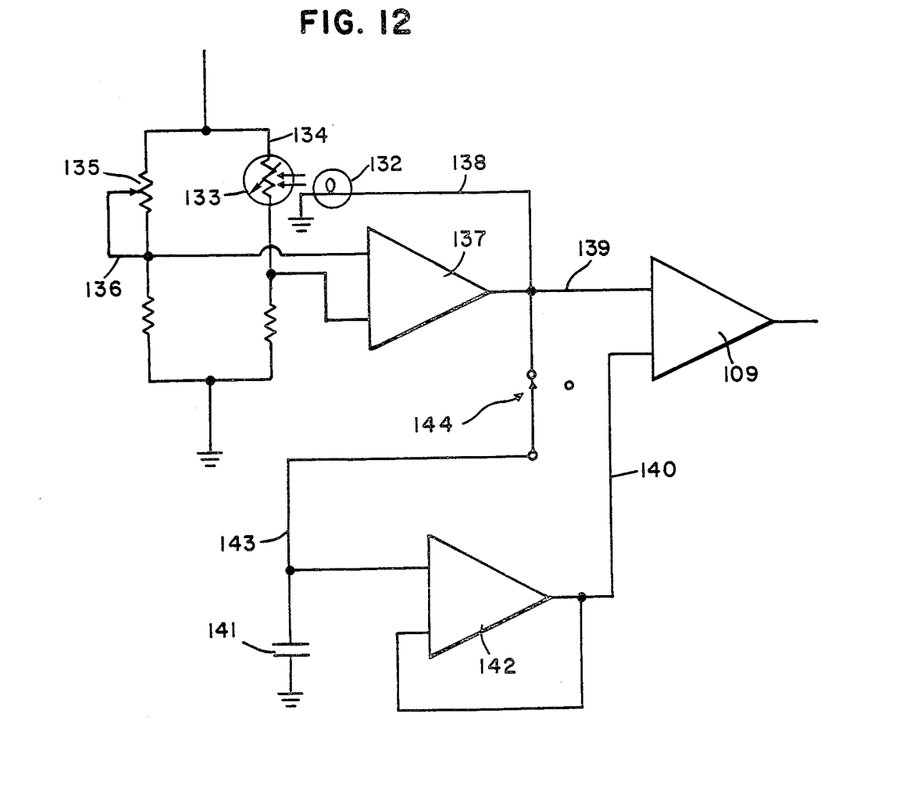
FIG. 12 is a schematic view of the fluorometer circuitry.
Figure 15:
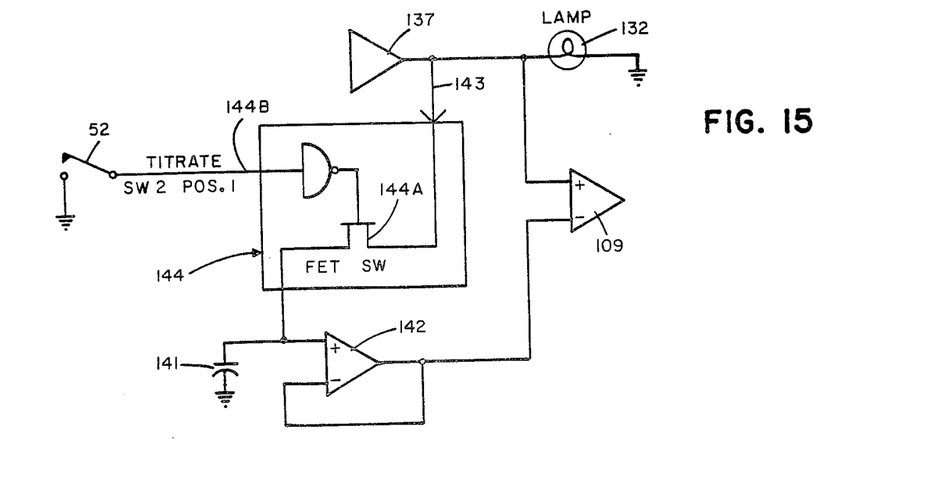
FIG. 15 is a schematic view of the switching means in the fluorometer circuitry.

5. Once the sample has been discharged into the cuvette 20, fluorescence results and the output circuit 129 of the fluorometer drives the pulse generator 105 until the desired end point of the titration is reached. Reference is made to FIGS. 12 and 15 in which the circuit 129 is detailed.

A third switch 130 when closed, sets the control 110 through a connection 131 so that the motor 31 will operate in an aspirating direction and the motor 28 is operated in a direction placing the pipette in its first position and through a connection 131A with the control 112 to ensure that the valve 34 has placed the buret in communication with the pipette. In practice, the switch 130 and its circuitry are provided to ensure that the pipette is in its first position before the switch 120 is operated.

From the foregoing, it will be appreciated that the circuitry provides, through the pairs of switches operated by the drives of the pipette, valve and buret, sequential operation of various conventional devices or control units to carry out the operation of the titrator as above described. While so much of the circuitry is obvious from the above that it is not completely detailed, certain sections of the circuitry are important and nonobvious.

Reference is first made to FIG. 12 wherein the lamp 132 of the fluorometer and its cell 133 are shown. The cell 133 is in a lead 134 and an adjustable resistor 135 is in a parallel lead 136, the leads 134 and 136 connected to an amplifier 137 of a type which increases the voltage of its output to the lamp lead 138 when or if the luminosity on the cell 133 decreases thereby enabling the cell 133 to be kept under a constant luminosity throughout a titration as the fluorescence decreases. The amplifier 137 is, in practice, one manufactured by Signetics Integrated Circuits Co. and identified as its model 5558 amplifier. The output of the amplifier 137 is also connected by a lead 139 to the end point detector 109 which is a voltage comparator to which a lead 140 is connected for the standard voltage.

An important feature of the invention is that the compensation is made for end point drift that would defeat accuracy, such drift being due to such causes as the decay of the calcein indicator, changes in temperature, slow release of metal ions from contaminants, and photolysis of the solution by the radiant energy. To accomplish this, the lead 140 includes a capacitor 141 and an adjustable amplifier 142 to establish the desired end point. Until the voltages match, the output of the comparator 109 is connected to the pulse generator 105.

The output of the amplifier 137 is also connected to the capacitor 141 by a lead 143 provided with a switch generally indicated at 144 and detailed in FIG. 15 wherein a normally closed FET switch 144A is held open when a lead 144B is closed during the time the pipette switch 52 is closed so that immediately after the end point is reached the capacitor 141 is charged with the voltage that existed at the end point. As a consequence, the next titration starts with that voltage at the comparator 109 ensuring that any drift in the end point is compensated for since each titration starts with the voltage prevailing at the end of the previous titration.

Figures 13, 14:
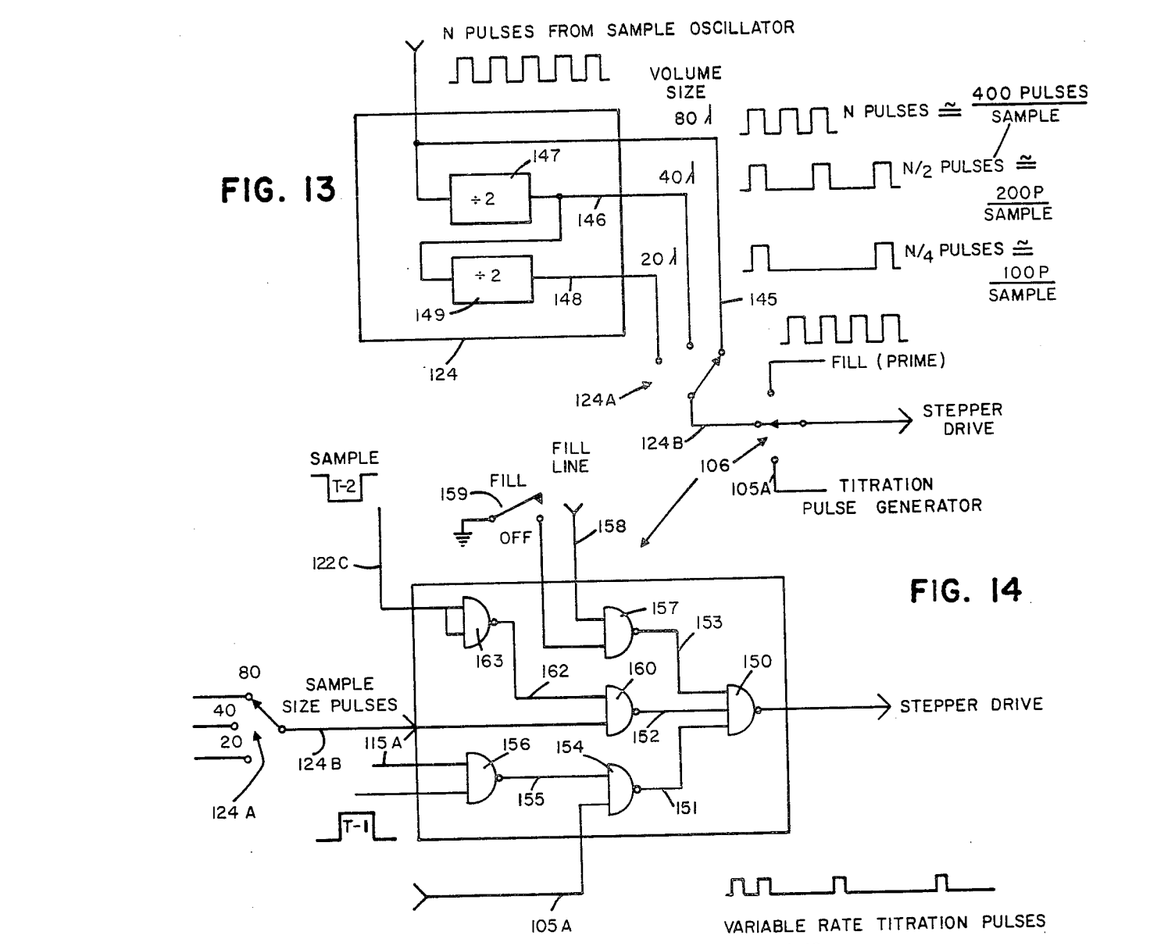
FIG. 13 is a schematic view of that part of the circuitry of the sample size selector.
FIG. 14 is a schematic view of the switching means between the oscillator, the sample size selector, and the pulse generator and the stepper motor.

While the drive 31A for the stepper motor 31 is thus controlled during a titration, the control of the stepper motor 31 at other times may best be seen in FIG. 13 wherein the sample size selection device 124 is shown as having a three position, manually operated switch 124A, one contact of which provides a direct connection 145 from the oscillator 115 delivering, when under the control of the timer 122, say, 400 pulses. A second contact provides a alternate connection 146 including a conventional unit 147 by which the number of pulses is divided by two thus providing 200 pulses to drive the stepper motor 31 to aspirate or deliver a smaller sample. A third switch contact is in a lead 148 containing a unit 149 identical to the unit 147 and connected to receive the pulse output thereof thus to further decrease the number of pulses that are available during the timed interval to drive the stepper motor 31 by one hundred pulses to provide a yet smaller sample.

The switch 106 is detailed in FIG. 14 and includes a gate 150 common to leads 151, 152, and 153. A gate 154 is operable to connect either the lead 105A from the pulse generator 105 to the gate 150 via the lead 151 or the lead 155 from a gate 156 thereto.

The lead 153 is under the control of a gate 157 in a lead 158 from the oscillator 115 and having a manually operated switch 159 closed when the buret 30 is to be filled and the titrator used, the lead 153 then closing the gate 150 relative to the leads 151 and 152.

A gate 160 controls the lead 152 when either the lead 124B from the switch 124A is conducting as it is whenever the timer 122 is energized and is opened, or when the lead 162 from the gate 163 is opened as it is when the lead 122C from the timer 122 is conducting. The gate 156 is under the control of a lead 115A to close the gate 154 relative to the lead 105A whenever the timer 122 is in service.

In practice, the ratio between the calcein and the potassium chloride is one part of calcein to the potassium chloride in the proximate range of from eight to twelve thousand parts. For best results, the grain size of the potassium chloride is in the range of from 20 to 40 mesh and the total weight of the chemicals is in the proximate range of from three hundred to five hundred milligrams for an average cuvette content of 25 ML.

To ensure best results, it is desirable that the users be supplied with the chemicals, the calcein and the potassium chloride, premixed in the cuvette and standard in weight and ratio and indicated at 20B, see FIG. 9A. To this end, each cuvette is provided with a closure, conveniently a snap-on cap 20C, and is packaged either individually or in convenient groupings in a sealed envelope 20D. Moisture causes calcein to deteriorate but the potassium chloride has greater affinity for water than the calcein and thus protects it. When a cuvette is to be used, it is opened and potassium hydroxide of 1 normal strength added to fill the cuvette to the indicated level L.

From the foregoing, it will be apparent that fluorometric titrators in accordance with the invention are well adapted to meet a wide range of requirements.

We claim:

1. A fluorometric titrator comprising a device operable to aspirate and subsequently discharge a sample, reversible means to transfer said device between first and second positions, sample control means to aspirate a precise sample volume into said device when in said first position and to discharge that volume in said second position, a fluorometer including a cuvette to receive the discharged volume and to hold a reagent that fluoresces when said sample volume is discharged therein, means to deliver chelating agent into said cuvette, a pulse generator controlled by the output of said fluorometer in response to resulting fluorescence to operate the delivery means for the chelating agent at a decreasing rate as the fluorescence is reduced and to produce an indication at the value of a chemical contained in the sample.

2. The fluorometric titrator of claim 1 in which the end point detector is also operable to control the return of the device to its first position.

3. The fluorometric titrator of claim 1 in which the fluorometer has a chamber opening both upwardly and downwardly, a holder detachably attached to the chamber closes the bottom of the opening and has a recess, and the cuvette is shaped and dimensioned to fit the recess thereby to be held in a predetermined position within the chamber.

4. The fluorometric titrator of claim 1 and means operable to render the end point of the detector substantially constant, at least after the first of a series of titrations.

5. The fluorometric titrator of claim 4 and means operable, at least after the first of a series of titrations to provide for each subsequent titration starting point having a substantially constant relation to the previous end point.

6. The fluorometric titrator of claim 5 in which the output circuit of the fluorometer includes the end point detector and means to increase the intensity of the lamp as the fluorescence is quenched to maintain the luminosity on the sensor of the fluorometer substantially constant.

7. The fluorometric titrator of claim 6 in which the means provide that the detector circuit always has a predetermined initial voltage at the start of a titration.

8. The fluorometric titrator of claim 1 in which the sample control means includes a pump and a reversible drive to operate said pump in either an aspirating or a delivering direction and means operable before the aspiration of a precise sample volume and before the discharge thereof to remove backlash from said pumping means.

9. The fluorometric titrator of claim 8 in which the pump and drive for the sample control means is also the delivery means for the chelating agent.

10. The fluorometric titrator of claim 9 in which the pump drive includes a reversible stepper motor and a transmission, and the means powered by the output of the fluorometer includes a pulse generator to drive the stepper motor during a titration and the sample control means includes an oscillator as an alternative drive for the stepper motor and means to time the operation of the oscillator in both the aspiration and the discharge of the precise sample volume.

11. The fluorometric titrator of claim 9 and means isolating the device from the pumping means during the operation of the backlash-removing means.

12. The fluorometric titrator of claim 11 and means operable during the return of said device and while it is connected to the pumping means to aspirate, into the device, a predetermined volume of air to provide a bubble as a barrier between the chelating agent and a sample and operable during the discharging stage to discharge said; bubble after the discharge of the sample volume.

13. The fluorometric titrator of claim 1 in which the delivery means is a pump operable both to aspirate and discharge fluids and to contain a sufficient volume of the chelating agent for at least one titration and has a drive including a reversible stepper motor, and there is a reservoir for the chelating agent, conduit means effecting communication between the delivery means, the device, and the reservoir and including a valve and reversible means to shift the valve between first and second positions, in the first, the device in communication with the pump and in the second, the reservoir and the pump in communication with each other, an oscillator as an alternative drive for said motor, and first and second timers as alternative means to power said oscillator, the sample control means includes the first timer, and means to energize said second timer to operate said pumping means to remove backlash from the delivery means before the sample concontrol means is operated in either position and also to aspirate chelating agent into the delivery means in the second valve position.

14. The fluorometric titrator of claim 13 and a chamber having top, front, side and end walls joined in a leakproof manner, the bottom of said chamber having at least one port, the pump, valve and device are located in the chamber, and the reversible drives therefor each supported by an appropriate one of said walls on the outside of said chamber.

15. The fluorometric titrator of claim 13 and a control circuit including switching means providing, after the operation of the sample control means to aspirate a precise sample volume and with the stepper motor set to operate the delivery means in a dispensing direction and the valve in its first position, three stages of operation, in the first, the transfer means operated to transfer the device to its second position and with the valve in its first position at the second position of the device and the sample control means then operated, in the second, the stepper motor driven by the pulse generator until the end point is detected, the direction of the motor then reversed to operate the delivery means in an aspirating direction and the valve is set in its second position, and in the third stage, energizing the stepper motor to aspirate the chelating agent from the reservoir, and then return the valve to its first position at least when the device is in its first position.

16. The fluorometric titrator of claim 15 in which the transfer means and the valve shifting means each include first and second switches for its first and second positions, respectively, and the delivery means also includes a switch operable when the pump contains an insufficient volume of the chelating agent, means operable during said first stage to set the valve in its second position with its second switch then operative to effect the energization of the second timer thereby to pump back to the reservoir enough chelating agent to remove backlash from the delivery means, the first switch of the pumping means then operable to effect the reverse operation of the valve shifting means before the second switch of the transfer means is closed, at the end of said second stage, the end point detector effects the direction of the stepper motor to drive the delivery means in an aspirating direction and the shifting of the valve into its second position thereby to energize the second timer unless and until the delivery means switch is operated, and the first switch of the transfer means, when closed, stopping the operation of the titrator.

17. The fluorometric titrator of claim 16 in which the delivery means also includes a second switch operable when the pumping means contains a predetermined maximum volume of the chelating agent, said second switch, when operated effects the setting of the valve in its first position, the first switch of the valve shifting means effecting the energization of the second timer whereby air is aspirated into the device as a barrier between the chelating agent and the next sample volume to be aspirated, the first switch of the transfer means when closed holding the second timer inoperative while the device is in its first position, and the second timer includes means operable when the device is in its second position to operate the second timer at the end of the interval provided by the first timer.

18. The fluorometric titrator of claim 16 in which the first position of the valve includes means, operable when the stepper motor is driven to effect the operation of the delivery means in an aspirating direction, to halt the transfer means between its two positions while the second timer is energized.

19. The fluorometric titrator of claim 16 and additional switch controlled means operable, when the switch thereof is closed, to set the direction the stepper motor will operate to drive the delivery means in an aspirating direction when energized and set the valve in its first position.

20. The fluorometric titrator of claim 1 in which value producing means is a readout responsive to the operation of the fluorometer to provide a value for the titration of a predetermined volume of a known value of a sample and means operable should the readout value be different than the known value to vary the operation of the sample control means so that it aspirates to vary the aspirated sample volume to provide a readout value to match said known value.

21. The fluorometric titrator of claim 20 and second means operable to vary the size of the aspirated sample volume independently of the means enabling readout and known values to be matched.

22. A fluorometric titrator comprising a device operable to aspirate and subsequently discharge a sample transferrable between first and second positions, sample control means operable to aspirate a precise sample volume into said device when in said first position and to discharge that volume with the device in said second position, a fluorometer including a cuvette to receive the discharged volume and to hold a reagent that fluoresces when the sample volume is discharged therein, means to deliver chelating agent into said cuvette, a pulse generator controlled by the output of said fluorometer in response to resulting fluorescence to operate the delivery means for the chelating agent at a decreasing rate as the fluorescence is reduced and to produce an indication of the value of a chemical contained in the sample.

23. The fluorometric titrator of claim 22 in which the sample control means includes pumping means in communication with the device, a reversible drive in control of said pumping means thereby to provide both for the aspiration of the sample volume and its discharge, an oscillator the output pulses of which said drive, and adjustable means to time the operation of the drive by the oscillator first with the drive operable to activate the pumping means in an aspirating direction and then in a discharging direction.

24. The fluorometric titrator of claim 23 and means to convert the output pulse output of the oscillator as determined by the timing means to at least one other and predetermined different number of output pulses whereby a different precise sample volume is aspirated and delivered without changing the timing means.

25. A fluorometric titrator comprising a device operable to aspirate and subsequently discharge a sample to contain a selected sample volume, reversible means to transfer said device between first and second positions, the first position the sample receiving position, sample control means to discharge that volume when the device is in said second position, a fluorometer including a cuvette to receive the discharged volume and to hold a reagent that fluoresces when said sample volume is discharged therein, means to deliver chelating agent into said cuvette, a pulse generator controlled by the output of said fluorometer in response to resulting fluorescence to operate the delivery means for the chelating agent at a decreasing rate as the fluorescence is reduced and to produce an indication of the value of a chemical contained in the sample.

26. The fluorometric titrator of claim 25 in which the reversible transfer means includes an arm and a reversible drive including a shaft in support of one end of the arm and operable to swing the arm through an arc from one position to the other and the device is supported by the other end of the arm to extend downwardly as the arm swings between the two positions of the device, and the transfer means includes means providing a predetermined angular disposition of said device at each of said positions.

27. The fluorometric titrator of claim 26 in which the device positioning means includes a gear train mounted on said arm, the device connected to the last gear of said train to turn therewith, a fixed gear coaxial with the shaft, and the first gear of the train in mesh with the fixed gear.

28. A fluorometric titrator comprising a fluorometer which yields an output, a cuvette for a fluorometric indicator solution, pumping means for a chelating agent including a delivery conduit in communication with the cuvette and operable to deliver a chelating agent thereto after a sample has been introduced into the cuvette to cause fluorescence, and delivery means controlled by the output of the fluorometer in response to the resulting fluorescence to operate the pumping means at a decreasing rate as the fluorescence is reduced, said pump means including a cylinder having an outlet at one end, a slidable piston having an axial bore opening towards the other end of the cylinder and including a fixed nut located at the open end of said bore, and the delivery means includes a motor, a drive shaft rotated thereby and including a threaded portion threaded through said nut and extending into said bore, the nut and shaft threads being of the micrometer type.

29. The fluorometric titrator of claim 28 in which the pumping means has a cylinder for the chelating agent and the piston includes an end portion that is a free fit in the cylinder and is of a uniform diameter throughout its cylinder-entering length thereby to function on a positive displacement basis.

30. A fluorometric titrator comprising a fluorometer which includes a sensor provided with an output circuit, a cuvette, a stirrer in the cuvette, the cuvette for a fluorescent indicator solution, pumping means for a chelating agent including a conduit in communication with the cuvette and operable to deliver the chelating agent thereto after a sample has been introduced into the cuvette that causes fluorescence, a drive for said pumping means including a stepper motor, the output circuit of the sensor of the fluorometer including a pulse generator operable to drive said motor and operating at a pulse-producing rate that decreases as the fluorescence is quenched and a detector opening said circuit when the fluorescence is reduced to a value selected as the end point of the test, said circuit also including means operable to adjust said end point to compensate for end point drift at least after the first of a series of titrations.

31. The fluorometric titrator of claim 30 in which the circuit includes voltage regulating means operable to increase the intensity of the fluorometer lamp as the fluorescence is quenched to maintain the luminosity on the sensor substantially constant.

32. The fluorometric titrator of claim 30 in which the end point detector is a voltage comparator, the output circuit of the fluorometer is connected thereto, a lead including a capacitor and an amplifier is connected to the comparator to provide the standard voltage with which the fluorometer output is compared with the comparator ending the titration when the voltages match, and switch means operable at the end of a titration to connect the output circuit to the capacitor to charge it whereby the next titration will have the voltage standard of the previous end point including any change or drift in the previous end point.

33. A fluorometric titrator comprising a fluorometer which yields an output and including a cell, a lamp and a cuvette between said cell and said lamp to receive a selected sample volume and adapted to hold a reagent that fluoresces when said sample volume is received therein, means to deliver chelating agent into said cuvette, a pulse generator controlled by the output of said fluorometer in response to resulting fluorescence to operate the delivery means for the chelating agent at a decreasing rate as the fluorescence is reduced, and means in control of said lamp and operable to maintain the cell luminosity at a constant level at least between the titrations.

34. The titrator of claim 33 in which the light control means is also operable in response to the decreasing cell luminosity to increase the lamp voltage to maintain, during a titration, the luminosity constant as the fluorescence decreases.

35. The titrator of claim 33 and means operable by the pulse generator to produce an indication of the value of a chemical contained in the sample.

36. In combination, a fluorometer having a chamber that opens downwardly and includes a holder detachably attached to the chamber to close the chamber opening and formed with a flat-surfaced recess, and a cuvette molded from a transparent material and dimensioned to fit the chamber and within the recess and be held in a predetermined position therein by the holder.

* * * * *